US011149279B2

(12) United States Patent
Savelieva

(10) Patent No.: US 11,149,279 B2
(45) Date of Patent: Oct. 19, 2021

(54) GENE THERAPY DNA VECTOR VTVAF17, METHOD OF PRODUCTION; *ESCHERICHIA COLI* STRAIN SCS110-AF, METHOD OF PRODUCTION; *ESCHERICHIA COLI* STRAIN SCS110-AF/VTVAF17 BEARING GENE THERAPY DNA VECTOR VTVAF17, METHOD OF PRODUCTION

(71) Applicants: CELL AND GENE THERAPY LTD, London (GB); OBSCHESTVO S OGRANICHENNOI OTVETSTVENNOSTJU "PRORYVNYE INNOVATSIONNYE TEKHNOLOGII", Moscow (RU)

(72) Inventor: Natalia Savelieva, Vienna (AT)

(73) Assignees: CELL AND GENE THERAPY LTD, London (GB); OBSCHESTVO S OGRANICHENNOI OTVETSTVENNOSTJU "PRORYVNYE INNOVATSIONNYE TEKHNOLOGII", Moscow (RU)

( * ) Notice: Subject to any disclaimer, the term of this patent is extended or adjusted under 35 U.S.C. 154(b) by 0 days.

(21) Appl. No.: 16/636,713

(22) PCT Filed: Mar. 26, 2018

(86) PCT No.: PCT/RU2018/000191
§ 371 (c)(1),
(2) Date: Feb. 5, 2020

(87) PCT Pub. No.: WO2019/039962
PCT Pub. Date: Feb. 28, 2019

(65) Prior Publication Data
US 2020/0385743 A1 Dec. 10, 2020

(30) Foreign Application Priority Data
Aug. 25, 2017 (RU) .......................... RU2017130215

(51) Int. Cl.
*C12N 15/69* (2006.01)
*C12N 9/14* (2006.01)
*C12N 15/70* (2006.01)
*C12R 1/19* (2006.01)

(52) U.S. Cl.
CPC ............. *C12N 15/69* (2013.01); *C12N 9/14* (2013.01); *C12N 15/70* (2013.01); *C12R 1/19* (2013.01)

(58) Field of Classification Search
CPC ................................ C12N 15/00; C12N 15/69
See application file for complete search history.

(56) References Cited

FOREIGN PATENT DOCUMENTS

WO 2003/044203 A2 5/2003

OTHER PUBLICATIONS

Carnes Aaron E. et al. Critical design criteria for minimal antibiotic-free plasmid vectors necessary to combine robust RNA Pol II and Pol III-mediated eukaryotic expression with high bacterial production yields. J Gene Med., 2010, 12(10):pp. 818-831.
Nelson EJR et al. Lentiviral vectors incorporating a human elongation factor 1a promoter for the treatment of canine eukocyte adhesion deficiency. Gene Ther, 2010, 17(5): pp. 672-677.
Hackett Perry B. Integrating DNA vectors for gene therapy. Mol Ther., 2007, 15(I):pp. 10-12.

*Primary Examiner* — Karen Cochrane Carlson
(74) *Attorney, Agent, or Firm* — Nadya Reingand; Yan Hankin

(57) ABSTRACT

Disclosed is a gene therapy DNA vector VTvaf17 for genetic modification of animal and human cells having SEQ ID No. 1, and methods for its synthesis, involving constructing vectors containing a promoter region of human elongation factor EF1A, a polylinker with sites for restriction endonucleases, a transcription terminator, a polyadenylation sequence of human growth factor, a regulatory element of transposon Tn10 allowing for antibiotic-free positive selection, an origin of replication, and a kanamycin resistance gene. *Escherichia coli* strain SCS110-AF is also provided by the present invention. The method for creating the strain involves constructing a linear DNA fragment containing regulatory element of transposon Tn10, a levansucrase gene, sacB, a chloramphenicol resistance gene, and two homologous sequences. The *E. coli* cells are transformed by electroporation and clones surviving chloramphenicol are chosen. The invention further discloses *Escherichia coli* strain SCS110-AF/VTvaf17, which carries DNA vector VTvaf17, and methods for its synthesis.

3 Claims, 9 Drawing Sheets
Specification includes a Sequence Listing.

pEGFP-C1    VTvaf17

FIG. 7    SEQ ID №1

EF1a promoter
CGTGAGGCTCCGGTGCCCGTCAGTGGGCAGAGCGCACATCGCCCACAGTCCCCGAGA
EF1a promoter
AGTTGGGGGGAGGGGTCGGCAATTGAACCGGTGCCTAGAGAAAGTGGCGCGGGGTAA
EF1a promoter
ACTGGGAAAGTGATGTCGTGTACTGGCTCCGCCTTTTTCCCGAGGGTGGGGGAGAAC
EF1a promoter
CGTATATAAGTGCAGTAGTCGCCGTGAACGTTCTTTTCGCAACGGGTTTGCCGCCA
EF1a promoter
GAACACAGGTAAGTGCCGTGTGTGGTTCCCGCGGGCCTGGCCTCTTTACGGGTTATG
EF1a promoter
GCCCTTGCGTGCCTTGAATTACTTCCACGCCCCTGGCTGCAGTACGTGATTCTTGAT
EF1a promoter
CCCGAGCTTCGGGTTGGAAGTGGGTGGGAGAGTTCGAGGCCTTGCGCTTAAGGAGCC
EF1a promoter
CCTTCGCCTCGTGCTTGAGTTGAGGCCTGGCTTGGGCGCTGGGGCCGCCGCGTGCGA
EF1a promoter
ATCTGGTGGCACCTTCGCGCCTGTCTCGCTGCTTTCGATAAGTCTCTAGCCATTTAA
EF1a promoter
AATTTTTGATGACCTGCTGCGACGCTTTTTTTCTGGCAAGATAGTCTTGTAAATGCG
EF1a promoter
GGCCAAGATCTGCACACTGGTATTTCGGTTTTTGGGGCCGCGGGCGGCGACGGGGCC
EF1a promoter
CGTGCGTCCCAGCGCACATGTTCGGCGAGGCGGGGCCTGCGAGCGCGGCCACCGAGA
EF1a promoter
ATCGGACGGGGGTAGTCTCAAGCTGGCCGGCCTGCTCTGGTGCCTGGCCTCGCGCCG
EF1a promoter
CCGTGTATCGCCCCGCCCTGGGCGGCAAGGCTGGCCCGGTCGGCACCAGTTGCGTGA
EF1a promoter
GCGGAAAGATGGCCGCTTCCCGGCCCTGCTGCAGGGAGCTCAAAATGGAGGACGCGG
EF1a promoter
CGCTCGGGAGAGCGGGCGGGTGAGTCACCCACACAAGGAAAAGGGCCTTTCCGTCC
EF1a promoter
TCAGCCGTCGCTTCATGTGACTCCACGGAGTACCGGGCGCCGTCCAGGCACCTCGAT
EF1a promoter
TAGTTCTCGAGCTTTTGGAGTACGTCGTCTTTAGGTTGGGGGGAGGGGTTTTATGCG
EF1a promoter
ATGGAGTTTCCCCACACTGAGTGGGTGGAGACTGAAGTTAGGCCAGCTTGGCACTTG
EF1a promoter
ATGTAATTCTCCTTGGAATTTGCCCTTTTTGAGTTTGGATCTTGGTTCATTCTCAAG
EF1a promoter
CCTCAGACAGTGGTTCAAAGTTTTTTCTTCCATTTCAGGTGTCGTGAAAACTACCC
MCS
CTAAAAGCCA*GGATCCGATATCGTCGACAAGCTTGGTACCGAATTC*CCTGTGACCCC
hGH TA
*TCCCCAGTGCCTCTCCTGGCCCTGGAAGTTGCCACTCCAGTGCCCACCAGCCTTGTC*
hGH TA
*CTAATAAAATTAAGTTGCATCATTTTGTCTGACTAGGTGTCCTTCTATAATATTATG*

FIG. 7 (cont'd)

hGH TA
*GGGTGGAGGGGGTGGTATGGAGCAAGGGGCAAGTTGGGAAGACAACCTGTAGGGCC*
hGH TA
*TGCGGGGTCTATTGGGAACCAAGCTGGAGTGCAGTGGCACAATCTTGGCTCACTGCA*
hGH TA
*ATCTCCGCCTCCTGGGTTCAAGCGATTCTCCTGCCTCAGCCTCCCGAGTTGTTGGGA*
hGH TA
*TTCCAGGCATGCATGACCAGGCTCAGCTAATTTTTGTTTTTTGGTAGAGACGGGGT*
hGH TA
*TTCACCATATTGGCCAGGCTGGTCTCCAACTCCTAATCTCAGGTGATCTACCCACCT*
hGH TA
*TGGCCTCCCAAATTGCTGGGATTACAGGCGTGAACCACTGCTCCCTTCCCTGTCCTT*
RNA out
ACGCGTAGAATTGGTAAAGAGAGTCGTGTAAAATATCGAGTTCGCACATCTTGTTGT
RNA out
CTGATTATTGATTTTTGGCGAAACCATTTGATCATATGACAAGATGTGTATCTACCT
RNA out                   ori
TAACTTAATGATTTTGATAAAAATCATTAACTAGTCCATGG<u>CTGCCTCGCGCGTTTC</u>
ori
<u>GGTGATGACGGTGAAAACCTCTGACACATGCAGCTCCCGGAGACGGTCACAGCTTGT</u>
ori
<u>CTGTAAGCGGATGCCGGGAGCAGACAAGCCCGTCAGGGCGCGTCAGCGGGTGTTGGC</u>
ori
<u>GGGTGTCGGGGCGCAGCCATGACCCAGTCACGTAGCGATAGCGGAGTGTATACTGGC</u>
ori
<u>TTAACTATGCGGCATCAGAGCAGATTGTACTGAGAGTGCACCATATGCGGTGTGAAA</u>
ori
<u>TACCGCACAGATGCGTAAGGAGAAAATACCGCATCAGGCGCTCTTCCGCTTCCTCGC</u>
ori
<u>TCACTGACTCGCTGCGCTCGGTCGTTCGGCTGCGGCGAGCGGTATCAGCTCACTCAA</u>
ori
<u>AGGCGGTAATACGGTTATCCACAGAATCAGGGGATAACGCAGGAAAGAACATGTGAG</u>
ori
<u>CAAAAGGCCAGCAAAAGGCCAGGAACCGTAAAAAGGCCGCGTTGCTGGCGTTTTTCC</u>
ori
<u>ATAGGCTCCGCCCCCCTGACGAGCATCACAAAAATCGACGCTCAAGTCAGAGGTGGC</u>
ori
<u>GAAACCCGACAGGACTATAAAGATACCAGGCGTTTCCCCCTGGAAGCTCCCTCGTGC</u>
ori
<u>GCTCTCCTGTTCCGACCCTGCCGCTTACCGGATACCTGTCCGCCTTTCTCCCTTCGG</u>
ori
<u>GAAGCGTGGCGCTTTCTCATAGCTCACGCTGTAGGTATCTCAGTTCGGTGTAGGTCG</u>
ori
<u>TTCGCTCCAAGCTGGGCTGTGTGCACGAACCCCCCGTTCAGCCCGACCGCTGCGCCT</u>
ori
<u>TATCCGGTAACTATCGTCTTGAGTCCAACCCGGTAAGACACGACTTATCGCCACTGG</u>
ori
<u>CAGCAGCCACTGGTAACAGGATTAGCAGAGCGAGGTATGTAGGCGGTGCTACAGAGT</u>
ori <u>TCTTGAAGTGGTGGCCTAACTACGGCTACACTAGAAGAACAGTATTTGGTATCTGCG</u>
ori
<u>CTCTGCTGAAGCCAGTTACCTTCGGAAAAGAGTTGGTAGCTCTTGATCCGGCAAAC</u>
ori
<u>AAACCACCGCTGGTAGCGGTGGTTTTTTTGTTTGCAAGCAGCAGATTACGCGCAGAA</u>
ori
<u>AAAAAGGATCTCAAGAAGATCCTTTGATCTTTTCTACGGGGTCTGACGCTCAGTGGA</u>
ori
<u>ACGAAAACTCACGTTAAGGGATTTTGGTCATGAGATTATCAAAAAGGATCTTCACCT</u>
ori
<u>AGATCCTTTTAAATTAAAAATGAAGTTTTAAATCAATCTAAAGTATATATGAGTAAA</u>
ori
<u>CTTGGTCTGACAGTTACCAATGCTTAATCAGTGAGGCACCTATCTCAGCGATCTGTC</u>
ori
<u>TATTTCGTTCATCCATAGTTGCCTGACTCC</u>

EF1a promoter — <u>underlined</u>
MCS — *bold italic*
hGH TA — <u>*underlined italic*</u>
RNA out — bold
ori — <u>underlined bold</u>

FIG. 7 (cont'd)

SEQUENCE LISTING

<160> NUMBER OF SEQ ID NOS: 37

<210> SEQ ID NO 1
<211> LENGTH: 3165
<212> TYPE: DNA
<213> ORGANISM: Homo Sapiens

<400> SEQUENCE: 1

```
cgtgaggctc cggtgcccgt cagtgggcag agcgcacatc gcccacagtc cccgagaagt      60 tgggggagg ggtcggcaat tgaaccggtg cctagagaaa gtgcgcggg gtaaactggg       120 aaagtgatgt cgtgtactgg ctccgccttt ttcccgaggg tggggagaa ccgtatataa      180 gtgcagtagt cgccgtgaac gttctttttc gcaacgggtt tgccgccaga acacaggtaa     240
gtgccgtgtg tggttcccgc gggcctggcc tctttacggg ttatgcccct tgcgtgcctt     300
gaattacttc cacgccctg gctgcagtac gtgattcttg atcccgagct tcgggttgga      360
agtgggtggg agagttcgag gccttgcgct taaggagccc cttcgcctcg tgcttgagtt     420
gaggcctggc ttgggcgctg gggccgccgc gtgcgaatct ggtggcacct tcgcgcctgt    480
ctcgctgctt tcgataagtc tctagccatt taaaattttt gatgacctgc tgcgacgctt    540
tttttctggc aagatagtct tgtaaatgcg ggccaagatc tgcacactgg tatttcggtt    600
tttggggccg cgggcggcga cggggcccgt gcgtcccagc gcacatgttc ggcgaggcgg     660
ggcctgcgag cgcggccacc gagaatcgga cggggtagt ctcaagctgg ccggcctgct    720
ctggtgcctg gcctcgcgcc gccgtgtatc gccccgccct gggcggcaag gctggcccgg    780
tcggcaccag ttgcgtgagc ggaaagatgg ccgcttcccg gccctgctgc agggagctca     840
aaatggagga cgcggcgctc gggagagcgg gcgggtgagt cacccacaca aaggaaaagg     900
gcctttccgt cctcagccgt cgcttcatgt gactccacgg agtaccgggc gccgtccagg     960
cacctcgatt agttctcgag cttttggagt acgtcgtctt taggttgggg ggaggggttt     1020
tatgcgatgg agtttcccca cactgagtgg gtggagactg aagttaggcc agcttggcac    1080
ttgatgtaat tctccttgga atttgccctt tttgagtttg gatcttggtt cattctcaag    1140
cctcagacag tggttcaaag ttttttttctt ccatttcagg tgtcgtgaaa actacccta    1200 aaagccagga tccgatatcg tcgacaagct tggtaccgaa ttccctgtga cccctcccca    1260
gtgcctctcc tggccctgga agttgccact ccagtgccca ccagccttgt cctaataaaa    1320
ttaagttgca tcattttgtc tgactaggtg tccttctata atattatggg gtggaggggg     1380
gtggtatgga gcaaggggca agtggggaag acaacctgta gggcctgcgg ggtctattgg    1440
```

| | |
|---|---|
| gaaccaagct ggagtgcagt ggcacaatct tggctcactg caatctccgc ctcctgggtt | 1500 |
| caagcgattc tcctgcctca gcctcccgag ttgtgggat tccaggcatg catgaccagg | 1560 |
| ctcagctaat ttttgttttt ttggtagaga cggggtttca ccatattggc caggctggtc | 1620 |
| tccaactcct aatctcaggt gatctaccca ccttggcctc ccaaattgct gggattacag | 1680 |
| gcgtgaacca ctgctccctt ccctgtcctt acgcgtagaa ttggtaaaga gagtcgtgta | 1740 |
| aaatatcgag ttcgcacatc ttgttgtctg attattgatt tttggcgaaa ccatttgatc | 1800 |
| atatgacaag atgtgtatct accttaactt aatgattttg ataaaaatca ttaactagtc | 1860 |
| catggctgcc tcgcgcgttt cggtgatgac ggtgaaaacc tctgacacat gcagctcccg | 1920 |
| gagacggtca cagcttgtct gtaagcggat gccgggagca gacaagcccg tcagggcgcg | 1980 |
| tcagcgggtg ttggcgggtg tcggggcgca gccatgaccc agtcacgtag cgatagcgga | 2040 |
| gtgtatactg gcttaactat gcggcatcag agcagattgt actgagagtg caccatatgc | 2100 |
| ggtgtgaaat accgcacaga tgcgtaagga gaaaataccg catcaggcgc tcttccgctt | 2160 |
| cctcgctcac tgactcgctg cgctcggtcg ttcggctgcg gcgagcggta tcagctcact | 2220 |
| caaaggcggt aatacggtta tccacagaat caggggataa cgcaggaaag aacatgtgag | 2280 |
| caaaaggcca gcaaaaggcc aggaaccgta aaaaggccgc gttgctggcg ttttccata | 2340 |
| ggctccgccc ccctgacgag catcacaaaa atcgacgctc aagtcagagg tggcgaaacc | 2400 |
| cgacaggact ataaagatac caggcgtttc ccctggaag ctcccgtg cgctctcctg | 2460 |
| ttccgaccct gccgcttacc ggatacctgt ccgcctttct cccttcggga agcgtggcgc | 2520 |
| tttctcatag ctcacgctgt aggtatctca gttcggtgta ggtcgttcgc tccaagctgg | 2580 |
| gctgtgtgca cgaaccccc gttcagcccg accgctgcgc cttatccggt aactatcgtc | 2640 |
| ttgagtccaa cccggtaaga cacgacttat cgccactggc agcagccact ggtaacagga | 2700 |
| ttagcagagc gaggtatgta ggcggtgcta cagagttctt gaagtggtgg cctaactacg | 2760 |
| gctacactag aagaacagta tttggtatct gcgctctgct gaagccagtt accttcggaa | 2820 |
| aaagagttgg tagctcttga tccggcaaac aaaccaccgc tggtagcggt ggtttttttg | 2880 |
| tttgcaagca gcagattacg cgcagaaaaa aaggatctca agaagatcct ttgatctttt | 2940 |
| ctacggggtc tgacgctcag tggaacgaaa actcacgtta agggattttg gtcatgagat | 3000 |
| tatcaaaaag gatcttcacc tagatccttt taaattaaaa atgaagtttt aaatcaatct | 3060 |
| aaagtatata tgagtaaact tggtctgaca gttaccaatg cttaatcagt gaggcaccta | 3120 |
| tctcagcgat ctgtctattt cgttcatcca tagttgcctg actcc | 3165 |

<210> SEQ ID NO 2
<211> LENGTH: 2175
<212> TYPE: DNA
<213> ORGANISM: Homo Sapiens

<400> SEQUENCE: 2

| | |
|---|---|
| atggcgggtc tgacggcggc ggccccgcgg cccggagtcc tcctgctcct gctgtccatc | 60 |
| ctccacccct ctcggcctgg aggggtccct ggggccattc tggtggagt tcctggagga | 120 |
| gtcttttatc caggggctgg tctcggagcc cttgaggag gagcgctggg gcctggaggc | 180 |
| aaacctctta agccagttcc cggagggctt gcgggtgctg gccttggggc agggctcggc | 240 |
| gccttccccg cagttacctt tccggggct ctggtgcctg gtggagtggc tgacgctgct | 300 |
| gcagcctata aagctgctaa ggctggcgct gggcttggtg gtgtcccagg agttggtggc | 360 |
| ttaggagtgt ctgcaggtgc ggtggttcct cagcctggag ccggagtgaa gcctgggaaa | 420 |

```
gtgccgggtg tggggctgcc aggtgtatac ccaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacaggggtt ggccccagg cagcagcagc agcggcagct     780
aaagcagcag caaagttcgg tgctggagca gccggagtcc tccctggtgt tggaggggct    840
ggtgttcctg gcgtgcctgg ggcaattcct ggaattggag gcatcgcagg cgttgggact    900
ccagctgcag ctgcagctgc agcagcagcc gctaaggcag ccaagtatgg agctgctgca    960
ggcttagtgc ctggtgggcc aggctttggc ccgggagtag ttggtgtccc aggagctggc   1020
gttccaggtg ttggtgtccc aggagctggg attccagttg tcccaggtgc tgggatccca   1080
ggtgctgcgg ttccaggggt tgtgtcacca gaagcagctg ctaaggcagc tgcaaaggca   1140
gccaaatacg gggccaggcc cggagtcgga gttggaggca ttcctactta cggggttgga   1200
gctgggggct ttcccggctt tggtgtcgga gtcggaggta tccctggagt cgcaggtgtc   1260
cctggtgtcg gaggtgttcc cggagtcgga ggtgtcccgg gagttggcat ttcccccgaa   1320
gctcaggcag cagctgccgc caaggctgcc aagtacggag tggggacccc agcagctgca   1380
gctgctaaag cagccgccaa agccgcccag tttgggttag ttcctggtgt cggcgtggct   1440
cctggagttg gcgtggctcc tggtgtcggt gtggctcctg gagttggctt ggctcctgga   1500
gttggcgtgg ctcctggagt tggtgtggct cctggcgttg gcgtggctcc cggcattggc   1560
cctggtggag ttgcagctgc agcaaaatcc gctgccaagg tggctgccaa agcccagctc   1620
cgagctgcag ctgggcttgg tgctggcatc cctggacttg gagttggtgt cggcgtccct   1680
ggacttggag ttggtgctgg tgttcctgga cttggagttg gtgctggtgt tcctggcttc   1740
ggggcagtac ctggagccct ggctgccgct aaagcagcca aatatggagc agcagtgcct   1800
ggggtccttg gagggctcgg ggctctcggt ggagtaggca tcccaggcgg tgtggtggga   1860
gccggacccg ccgccgccgc tgccgcagcc aaagctgctg ccaaagccgc ccagtttggc   1920
ctagtgggag ccgctgggct cggaggactc ggagtcggag ggcttggagt tccaggtgtt   1980 ggggccttg gaggtatacc tccagctgca gccgctaaag cagctaaata cggtgctgct    2040
ggccttggag gtgtcctagg gggtgccggg cagttcccac ttggaggagt ggcagcaaga   2100
cctggcttcg gattgtctcc cattttccca ggtgggcct gcctggggaa agcttgtggc    2160
cggaagagaa aatga                                                    2175
```

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide ORI-F

<400> SEQUENCE: 3
agtccatggc tgcctcgcgc gtttcg                                          26

<210> SEQ ID NO 4
<211> LENGTH: 26
<212> TYPE: DNA
<213> ORGANISM: Artificial Sequence
<220> FEATURE:

<223> OTHER INFORMATION: Oligonucleotide ORI-R

<400> SEQUENCE: 4
agcctcacgg gagtcaggca actatg                                           26

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide Ori-M1

<400> SEQUENCE: 5
ctacactaga agaacagtat ttg                                              23

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide Ori-M2

<400> SEQUENCE: 6
caaatactgt tcttctagtg tag                                              23

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide EF1-F

<400> SEQUENCE: 7
cctgactccc gtgaggctcc ggtgcc                                           26

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide EF1-R

<400> SEQUENCE: 8
tcggatcctg gcttttaggg gtagttttc                                        29

<210> SEQ ID NO 9
<211> LENGTH: 31
<212> TYPE: DNA
<213> ORGANISM: Artificial Sequence
<220> FEATURE:
<223> OTHER INFORMATION: Oligonucleotide hGH-F

<400> SEQUENCE: 9
aggatccgaa ttccctgtga cccctcccca g                                     31

<210> SEQ ID NO 10
<211> LENGTH: 40
<212> TYPE: DNA
<213> ORGANISM: Artificial Sequence
<220> FEATURE:
<223> OTHER INFORMATION: Oligonucleotide hGH-R

<400> SEQUENCE: 10
ctctttacca attctacgcg taaggacagg gaagggagca                            40

```
<210> SEQ ID NO 11
<211> LENGTH: 40
<212> TYPE: DNA
<213> ORGANISM: Artificial Sequence
<220> FEATURE:
<223> OTHER INFORMATION: Oligonucleotide RO-F

<400> SEQUENCE: 11
cttccctgtc cttacgcgta gaattggtaa agagagtcgt                              40

<210> SEQ ID NO 12
<211> LENGTH: 41
<212> TYPE: DNA
<213> ORGANISM: Artificial Sequence
<220> FEATURE:
<223> OTHER INFORMATION: Oligonucleotide RO-R

<400> SEQUENCE: 12
ccgtagaaaa ctagttaatg atttttatca aaatcattaa g                            41

<210> SEQ ID NO 13
<211> LENGTH: 49
<212> TYPE: DNA
<213> ORGANISM: Artificial Sequence
<220> FEATURE:
<223> OTHER INFORMATION: Oligonucleotide RO-1

<400> SEQUENCE: 13
gaattggtaa agagagtcgt gtaaaatatc gagttcgcac atcttgttg                    49

<210> SEQ ID NO 14
<211> LENGTH: 47
<212> TYPE: DNA
<213> ORGANISM: Artificial Sequence
<220> FEATURE:
<223> OTHER INFORMATION: Oligonucleotide RO-2

<400> SEQUENCE: 14
gatttttggc gaaaccattt gatcatatga caagatgtgt atctacc                      47

<210> SEQ ID NO 15
<211> LENGTH: 47
<212> TYPE: DNA
<213> ORGANISM: Artificial Sequence
<220> FEATURE:
<223> OTHER INFORMATION: Oligonucleotide RO-3

<400> SEQUENCE: 15
atgattttta tcaaaatcat taagttaagg tagatacaca tcttgtc                      47

<210> SEQ ID NO 16
<211> LENGTH: 34
<212> TYPE: DNA
<213> ORGANISM: Artificial Sequence
<220> FEATURE:
<223> OTHER INFORMATION: Oligonucleotide Kan-F

<400> SEQUENCE: 16
aaatcattaa ctagttttct acggggtctg acgc                                    34

<210> SEQ ID NO 17
<211> LENGTH: 33
<212> TYPE: DNA
<213> ORGANISM: Artificial Sequence
<220> FEATURE:
<223> OTHER INFORMATION: Oligonucleotide Kan-R
```

<400> SEQUENCE: 17
cagccatgga ctagtggtgg cacttttcgg gga                                    33

<210> SEQ ID NO 18
<211> LENGTH: 30
<212> TYPE: DNA
<213> ORGANISM: Artificial Sequence
<220> FEATURE:
<223> OTHER INFORMATION: Oligonucleotide MCS1

<400> SEQUENCE: 18
gatccgatat cgtcgacaag cttggtaccg                                        30

<210> SEQ ID NO 19
<211> LENGTH: 30
<212> TYPE: DNA
<213> ORGANISM: Artificial Sequence
<220> FEATURE:
<223> OTHER INFORMATION: Oligonucleotide MCS2

<400> SEQUENCE: 19
aattcggtac caagcttgtc gacgatatcg                                        30

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide LHA-F

<400> SEQUENCE: 20
gctgacgctg caggtgatc                                                    19

<210> SEQ ID NO 21
<211> LENGTH: 38
<212> TYPE: DNA
<213> ORGANISM: Artificial Sequence
<220> FEATURE:
<223> OTHER INFORMATION: Oligonucleotide LHA-R

<400> SEQUENCE: 21
gacaagatgt gtgtctaccg cttcaggtta cccgccag                               38

<210> SEQ ID NO 22
<211> LENGTH: 38
<212> TYPE: DNA
<213> ORGANISM: Artificial Sequence
<220> FEATURE:
<223> OTHER INFORMATION: Oligonucleotide IN-F

<400> SEQUENCE: 22
ctggcgggta acctgaagcg gtagacacac atcttgtc                               38

<210> SEQ ID NO 23
<211> LENGTH: 42
<212> TYPE: DNA
<213> ORGANISM: Artificial Sequence
<220> FEATURE:
<223> OTHER INFORMATION: Oligonucleotide IN-1

<400> SEQUENCE: 23
atttttggcg aaaccattct atcatatgac aagatgtgtg tc                          42

<210> SEQ ID NO 24
<211> LENGTH: 42

<212> TYPE: DNA
<213> ORGANISM: Artificial Sequence
<220> FEATURE:
<223> OTHER INFORMATION: Oligonucleotide IN-2

<400> SEQUENCE: 24
atatgataga atggtttcgc caaaaatcaa taatcagaca ac          42

<210> SEQ ID NO 25
<211> LENGTH: 37
<212> TYPE: DNA
<213> ORGANISM: Artificial Sequence
<220> FEATURE:
<223> OTHER INFORMATION: Oligonucleotide IN-R

<400> SEQUENCE: 25
caaacttttt gatgttcatc ttgttgtctg attattg               37

<210> SEQ ID NO 26
<211> LENGTH: 37
<212> TYPE: DNA
<213> ORGANISM: Artificial Sequence
<220> FEATURE:
<223> OTHER INFORMATION: Oligonucleotide SacB-F

<400> SEQUENCE: 26
caataatcag acaacaagat gaacatcaaa aagtttg               37

<210> SEQ ID NO 27
<211> LENGTH: 38
<212> TYPE: DNA
<213> ORGANISM: Artificial Sequence
<220> FEATURE:
<223> OTHER INFORMATION: Oligonucleotide SacB-R

<400> SEQUENCE: 27
cttacgtgcc gatcattatt tgttaactgt taattgtc              38

<210> SEQ ID NO 28
<211> LENGTH: 39
<212> TYPE: DNA
<213> ORGANISM: Artificial Sequence
<220> FEATURE:
<223> OTHER INFORMATION: Oligonucleotide CatR-F

<400> SEQUENCE: 28
caattaacag ttaacaaata atgatcggca cgtaagagg             39

<210> SEQ ID NO 29
<211> LENGTH: 39
<212> TYPE: DNA
<213> ORGANISM: Artificial Sequence
<220> FEATURE:
<223> OTHER INFORMATION: Oligonucleotide CatR-R

<400> SEQUENCE: 29
cgagacgaac agaggcgtag ttacgccccg ccctgccac             39

<210> SEQ ID NO 30
<211> LENGTH: 39
<212> TYPE: DNA
<213> ORGANISM: Artificial Sequence
<220> FEATURE:
<223> OTHER INFORMATION: Oligonucleotide RHA-F

<400> SEQUENCE: 30

```
tggcagggcg gggcgtaact acgcctctgt tcgtctcga                                  39
```

```
<210> SEQ ID NO 31
<211> LENGTH: 20
<212> TYPE: DNA
<213> ORGANISM: Artificial Sequence
<220> FEATURE:
<223> OTHER INFORMATION: Oligonucleotide RHA-R

<400> SEQUENCE: 31
ctcagcagca actcacgtac                                                       20
```

```
<210> SEQ ID NO 32
<211> LENGTH: 29
<212> TYPE: DNA
<213> ORGANISM: Artificial Sequence
<220> FEATURE:
<223> OTHER INFORMATION: Oligonucleotide MVGFP-F

<400> SEQUENCE: 32
ggatccatgg tgagcaaggg cgaggagct                                             29
```

```
<210> SEQ ID NO 33
<211> LENGTH: 28
<212> TYPE: DNA
<213> ORGANISM: Artificial Sequence
<220> FEATURE:
<223> OTHER INFORMATION: Oligonucleotide MVGFP-R

<400> SEQUENCE: 33
gaatcctcac aaatttgta atccagag                                               28
```

```
<210> SEQ ID NO 34
<211> LENGTH: 22
<212> TYPE: DNA
<213> ORGANISM: Artificial Sequence
<220> FEATURE:
<223> OTHER INFORMATION: Oligonucleotide ELN-F

<400> SEQUENCE: 34
ggatccatgg cgggtctgac gg                                                    22
```

```
<210> SEQ ID NO 35
<211> LENGTH: 26
<212> TYPE: DNA
<213> ORGANISM: Artificial Sequence
<220> FEATURE:
<223> OTHER INFORMATION: Oligonucleotide ELN-R

<400> SEQUENCE: 35
gaatcctcat tttctcttcc ggccac                                                26
```

```
<210> SEQ ID NO 36
<211> LENGTH: 25
<212> TYPE: DNA
<213> ORGANISM: Artificial Sequence
<220> FEATURE:
<223> OTHER INFORMATION: Oligonucleotide EL1F

<400> SEQUENCE: 36
gagtcctcct gctcctgctg tccat                                                 25
```

```
<210> SEQ ID NO 37
<211> LENGTH: 22
<212> TYPE: DNA
<213> ORGANISM: Artificial Sequence
```

```
<220> FEATURE:
<223> OTHER INFORMATION: Oligonucleotide EL1R

<400> SEQUENCE: 37
aaaggtaact gcggggaagg cg                                              22
```

GENE THERAPY DNA VECTOR VTVAF17, METHOD OF PRODUCTION; ESCHERICHIA COLI STRAIN SCS110-AF, METHOD OF PRODUCTION; ESCHERICHIA COLI STRAIN SCS110-AF/VTVAF17 BEARING GENE THERAPY DNA VECTOR VTVAF17, METHOD OF PRODUCTION

CROSS-REFERENCE TO RELATED APPLICATIONS

The present patent application is a National stage application for PCT application PCT/RU2018/000191 filed Mar. 26, 2018 which claims priority to Russian patent application RU2017130215 filed Aug. 25, 2017 all of which are fully incorporated here by reference.

FIELD OF THE INVENTION

The invention refers to genetic engineering and can be used in biotechnology, medicine and agriculture for the manufacture of gene therapy products. That is, the produced gene therapy DNA vector containing the target gene can be delivered to the cells of human beings and animals that experience reduced or insufficient expression of that gene, thus ensuring the desired therapeutic effect.

REFERENCE TO A SEQUENCE LISTING

Sequence Listing IDs 1 through 37 (i.e., SEQ ID NO: 1 through SEQ ID NO: 37), incorporated fully by reference herein, are provided in ASCII format together in one separately enclosed .TXT file, submitted via EFS-Web—File name: SEQUENCELISTING_ASCII_16-636713_Revised37.txt; Date of Creation: Monday, Apr. 27, 2020; File size: 13.6 KB.

BACKGROUND OF THE INVENTION

Gene therapy is an innovative approach in medicine aimed at treating inherited and acquired diseases by means of delivery of new genetic material into a patient's cells to compensate for or suppress the function of a mutant gene and/or treat a genetic disorder.

Transporters of genetic material (gene therapy vectors) are divided into viral and nonviral vectors. The most efficient viral vectors include retroviruses, lentiviruses, adeno-associated viruses (AAV), herpesviruses, poxviruses, and adenoviruses (Lukashev A N, Zamyatnin A A Jr. Viral Vectors for Gene Therapy: Current State and Clinical Perspectives. Biochemistry (Mosc). 2016. 81:700-708.). Nonviral delivery of genetic material predominantly involves plasmids bearing a therapeutic gene and combined with various carriers such as lipids, cationic polymers, dendrimers, polypeptides, and nanoparticles (Mintzer M A, Simanek E E. Nonviral vectors for gene delivery. Chem Rev. 2009. 109:259-302).

Despite a virus being naturally almost an ideal agent for the delivery of recombinant DNA into the cell, in terms of both speed and efficiency, there are some practical limitations to the use of viral delivery systems. These include manufacturing challenges, lack of selectivity, immune response, potential carcinogenic risks, as well as inflammation following transduction. Some of these problems are yet to be solved. This is why lately gene therapy has paid increasingly more attention to the development of nonviral gene delivery systems.

Plasmid is an autonomously replicating extrachromosomal circular DNA. Plasmids may contain genes of resistance to antibiotics, heavy metal ions, and genes controlling catabolism of some organic compounds (Lipps G. (editor). (2008). Plasmids: Current Research and Future Trends. Caister Academic Press. ISBN 978-1-904455-35-6). As mobile genetic elements, plasmids are capable of being transmitted from one bacterial cell to another by conjugation, thus facilitating horizontal gene transfer.

Plasmids are free of limitations inherent in viral vectors. In the target cell, they exist as an episome without being integrated into the genome, while producing them is quite cheap, and there is no immune response or side effects caused by the administration of plasmids, which makes them a convenient tool for gene therapy (transfer of therapeutic genes) and prevention of the genetic diseases (DNA vaccination) (Li L, Petrovsky N. Molecular mechanisms for enhanced DNA vaccine immunogenicity. Expert Rev Vaccines. 2016; 15(3):313-29).

Other than being quite a promising means of delivery in gene therapy, plasmids have long been instrumental in laboratories specializing in molecular biology and other biotechnology, and have been applied successfully in molecular cloning and the development of recombinant proteins (Russell, David W.; Sambrook, Joseph (2001), Molecular cloning: a laboratory manual. Cold Spring Harbor, N.Y; Cold Spring Harbor Laboratory)

Despite the obvious prospects for gene therapy, a critical limitation to the use of plasmids as therapeutic agents is that they contain: i) genes of resistance to antibiotics for the development of constructs in carrying strains, ii) various regulatory elements represented by sequences of viral genomes. Another limitation is the size of therapeutic plasmids which determines the efficiency of vector delivery to the target cell.

It is commonly known that over the past years the entire world has been witnessing increasingly growing resistance of infectious agents to antimicrobial drugs. The development of antimicrobial resistance is a natural biological response to antibiotics which cause selective pressure facilitating the selection, survival and growth of resistant strains of microorganisms. Resistance to antibiotics is of great social and economic importance and is considered to be a threat to national security (MacPherson D. W., Gushulak B. D., Baine W. B., Bala S., Gubbins P. O., Holtom P., Segarra-Newnham M. 2009. Population mobility, globalization, and antimicrobial drug resistance. Emerg Infect Dis 15:1727-1732). It is plasmids that ensure horizontal transfer of genes, including antibiotic resistance genes, inside a micropopulation, which gives them a selective advantage. Therefore, the growth of human infectious agents resistant to present-day antibiotics is attributed to horizontal gene transfer (Ramirez M S, Traglia G M, Lin D L, Tran T, Tolmasky M E. Plasmid-Mediated Antibiotic Resistance and Virulence in Gram-Negatives: the *Klebsiella pneumoniae* Paradigm. Microbiol Spectr. 2014 (5).

For this reason, the European Medicines Agency deems it necessary to refrain from adding antibiotic resistance marker genes to newly engineered plasmids for gene therapy (Reflection paper on design modifications of gene therapy medicinal products during development/14 Dec. 2011 EMA/CAT/GTWP/44236/2009 Committee for advanced therapies).

One more significant limitation to the use of therapeutic plasmid vectors is that they contain regulatory elements to increase the expression of target genes (promoters, enhancers, post-translational regulatory elements), which are mainly represented by nucleotide sequences of genomes of various viruses (Draft Guideline on the quality, non-clinical and clinical aspects of gene therapy medicinal products, www.ema.europa.eu).

Another disadvantage of existing plasmid vectors for gene therapy is their size (length). It is known that the greater the length of plasmid, the less efficiently it penetrates the target cell. Existing plasmids often have unnecessary, non-functional sites that increase their length substantially (Mairhofer J, Grabherr R. Rational vector design for efficient non-viral gene delivery: challenges facing the use of plasmid DNA. Mol Biotechnol. 2008.39(2):97-104).

A method has been known for accumulating plasmids in *Escherichia coli* strains without using antibiotics (Cranenburgh R M, Hanak J A, Williams S G, Sherratt D J. *Escherichia coli* strains that allow antibiotic-free plasmid selection and maintenance by repressor titration. Nucleic Acids Res. 2001. 29(5):E26). DH1lacdapD and DH1lacP2dapD strains of *Escherichia coli* were constructed, where gene dapD encoding enzyme 2,3,4,5-tetrahydropyridine-2,6-dicarboxylate-N-succinyltransferase involved in the biosynthesis of L-lysine is controlled by the lac promoter. In the absence of the inducer IPTG (Isopropyl-B-D-1-thiogalactopyranoside), these strains are subject to lysis. However, the administration of the multicopy plasmid pORT containing the lac operon induces expression of gene dapD, and, therefore, transformed clones may be picked out and reproduced. These strains, however, are characterized by low levels and instability of transformation.

Furthermore, a method has been known for constructing *Escherichia coli* strains for the development of plasmids in an antibiotic-free plasmid selection system (Mairhofer J, Pfaffenzeller I, Merz D, Grabherr R. A novel antibiotic free plasmid selection system: advances in safe and efficient DNA therapy. Biotechnol J. 2008. 3(1):83-89). The selected bacterial strains (e.g., DG5α, JM109, MG1655) were modified in such a way that plasmid replication inhibitor RNA I could suppress the translation of genes essential for bacterial activity (for example, murA encoding the enzyme UDP-N-acetylglucosamine 1-carboxyvinyl-transferase involved in the biosynthesis of bacterial cell wall peptidoglycan) by forming a duplex of RNA/antisense RNA. Gene murA was controlled by repressor protein tetR and could only be expressed in the presence of the constructed RNA 1-carrying plasmid. However, it was discovered that adding IPTG would result in the production of *Escherichia coli* colonies free of the target plasmid vector. The mechanism of selection inhibition remains unknown.

Likewise, a method has been known for constructing vectors of the smallest length. A small supercoiled DNA molecule was engineered which is devoid of all prokaryotic nucleotide sequences and contains only origins of replication and the antibiotic resistance gene (the so-called "minicircle"). The vector was produced by integrase-mediated intramolecular integration using phage φC31 (Chen Z Y, He C Y, Ehrhardt A, Kay M A. Minicircle DNA vectors devoid of bacterial DNA result in persistent and high-level transgene expression in vivo. Mol Ther. 2003. 8(3):495-500). The disadvantages of such plasmid vectors include the complexity of their production and the impossibility to construct them on an industrial scale.

An invention is reported in Patent Application No. US 2011152377/10 which describes preparation of an expression construct without the resistance to antibiotics which contains a polynucleotide encoding the repressor protein. The expression of the said repressor protein regulates the expression of the toxic gene product integrated into the region of the *E. coli* genome. However, like any other method of selection based on the use of repressor proteins, this method is characterized by unstable and inefficient transformation.

U.S. Pat. No. 9,644,211 describes a method for producing a vector of the smallest length ("minicircle"). This vector does not contain prokaryotes and is produced by parA-mediated recombination in a cultured *E. coli* strain. The disadvantage of this method of producing the shortest vector is the impossibility to use it on an industrial scale.

The prototype of this invention in terms of the use of recombinant DNA vectors for gene therapy is the method of producing a recombinant vector for genetic immunization (U.S. Pat. No. 9,550,998). The plasmid vector is a supercoiled plasmid DNA vector which is used for the expression of cloned genes in human and animal cells. The vector contains an origin of replication, regulatory elements comprising human cytomegalovirus promoter and enhancer, and regulatory sequences from the human T-cell lymphotropic virus.

The vector is accumulated in a dedicated *E. coli* strain free of antibiotics through antisense complementation of gene sacB administered into the strain by means of bacteriophage. The use of this DNA vector in gene therapy is limited by the presence of regulatory sequences of viral genomes.

SUMMARY

The purpose of this invention is to construct a gene therapy DNA vector for genetic modification of human and animal cells, which would reasonably combine the following:

I) possibility of safe use in the gene therapy of human beings and animals due to the absence of antibiotic resistance genes in the gene therapy DNA vector;

II) length that ensures efficient gene delivery to the target cell;

III) presence of regulatory elements that ensure efficient expression of the target genes while not being represented by nucleotide sequences of viral genomes;

IV) producibility and constructability on an industrial scale.

Item I is critical and is provided herein in compliance with the requirements of the state regulators for gene therapy medicines and, specifically, the requirement of the European Medicines Agency to refrain from adding antibiotic resistance marker genes to newly engineered plasmids for gene therapy (Reflection paper on design modifications of gene therapy medicinal products during development/14 Dec. 2011 EMA/CAT/GTWP/44236/2009 Committee for advanced therapies).

The specified purpose is achieved by first constructing 3165-bp gene therapy DNA vector VTvaf17 for genetic modification of animal and human cells containing nucleotide sequence SEQ ID NO: 1. The method of constructing 3165-bp gene therapy DNA vector VTvaf17 involves, first of all, constructing a 4182-bp vector at the next stage that contains a 1188-bp promoter region of human elongation factor EF1A with an intrinsic enhancer, a 35-bp polylinker with sites for restriction endonucleases BamHI, EcoRV, SalI, Hindi", KpnI, EcoRI, a 466-bp transcription terminator and a polyadenylation sequence of the human growth hormone, a 136-bp regulatory element RNA-OUT of transposon Tn10 allowing for antibiotic-free positive selection, a 1299-bp origin of replication for autonomous replication with a single nucleotide substitution to increase vector production in the cells of most *Escherichia coli* strains, a 1010-bp kanamycin resistance gene, and then it is cleaved by SpeI restriction sites, and the remaining fragment is ligated to itself. The specified purpose is achieved by obtaining *Escherichia coli* strain SCS110-AF for the production of gene therapy DNA vector VTvaf17 or gene therapy DNA vectors based on it allowing for antibiotic-free positive selection. The method of obtaining *Escherichia coli* strain SCS 110-AF for the production of gene therapy DNA vector VTvaf17 or gene therapy DNA vectors based on it involves constructing a 64-bp linear DNA fragment which contains regulatory element RNA-IN of transposon Tn10 allowing for antibiotic-free positive selection, 1422-bp levansucrase gene sacB the product of which ensures selection within a sucrose-containing medium, 763-bp chloramphenicol resistance gene catR required for the picking of strain clones in which homologous recombination occurs, and two homologous sequences, 329-bp and 233-bp, ensuring homologous recombination in the region of gene recA concurrent with gene inactivation, and then the *Escherichia coli* cells are transformed by electroporation, and clones surviving in a medium containing 10 µg/ml of chloramphenicol are picked. *Escherichia coli* strain SCS110-AF/VTvaf17 (registered at the Russian National Collection of Industrial Microorganisms under number B-12990, INTERNATIONAL DEPOSITARY AUTHORITY No. NCIMB 42801) carrying gene therapy DNA vector VTvaf17 is also constructed for its further development allowing for antibiotic-free selection. The method of obtaining *Escherichia coli* strain SCS110-AF/VTvaf17 (registered at the Russian National Collection of Industrial Microorganisms under number B-12990, INTERNATIONAL DEPOSITARY AUTHORITY No. NCIMB 42801) carrying gene therapy DNA vector VTvaf17 involves making electrocompetent cells of *Escherichia coli* strain SCS110-AF and subjecting these cells to electroporation with gene therapy DNA vector VTvaf17. After that, the cells are poured into agar plates (Petri dishes) with a selective medium containing yeastrel, peptone, 6% sucrose, and 10 µg/ml of chloramphenicol.

BRIEF DESCRIPTION OF THE DRAWINGS

The essence of the invention is explained in the drawings, where

FIG. 7 shows the same DNA vector, marked up to show its structural elements, as explained below.

FIG. 1 marks the following structural elements of the vector:
(1) EF1a (1 to 1188 bp)—the promoter region of human elongation factor EF1A with an intrinsic enhancer contained in the first intron of the gene. It ensures efficient transcription of the recombinant gene in most human tissues.
(2) MCS (1208 to 1243 bp)—the polylinker (multiple cloning site) which contains a sequence of restriction enzymes BamHI, EcoRV, SalI, HindIII, KpnI, and EcoRI and allows cloning the target therapeutic genes.
(3) hGH-TA (1244 to 1710 bp)—the transcription terminator and the polyadenylation sequence of the human growth hormone gene.
(4) RNA-out (1717 to 1853 bp)—the regulatory element RNA-OUT of transposon Tn 10 allowing for antibiotic-free positive selection in case of the use of *Escherichia coli* strain SCS 110.
(5) ori (1866 to 3165 bp)—the origin of replication for autonomous replication with a single nucleotide substitution to increase plasmid production in the cells of most *Escherichia coli* strains.

The linear fragment consists of a cassette carrying the regulatory element RNA-IN of transposon Tn10 for antibiotic-free selection (64 bp), levansucrase gene sacB the product of which ensures selection within a sucrose-containing medium (1422 bp), and chloramphenicol resistance gene catR required for the picking of strain clones in which homologous recombination occurred (763 bp). The cassette is flanked by two homology arms that ensure the process of recombination in the region of gene recA with concurrent gene inactivation (329-bp and 233-bp for the left arm and for the right arm, respectively).

Figure 1:
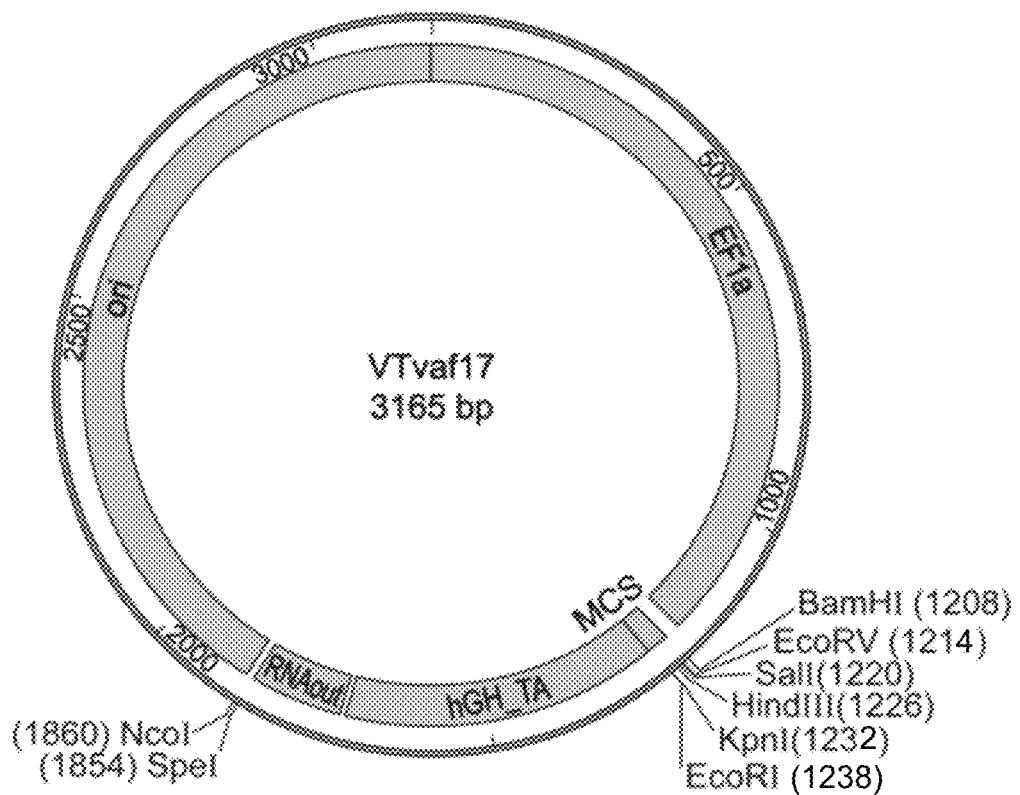
FIG. 1 shows the structure of gene therapy DNA vector VTvaf17, which is a 3165-bp circular double-strand DNA molecule capable of autonomous replication in *Escherichia coli* cells.
Figure 2:
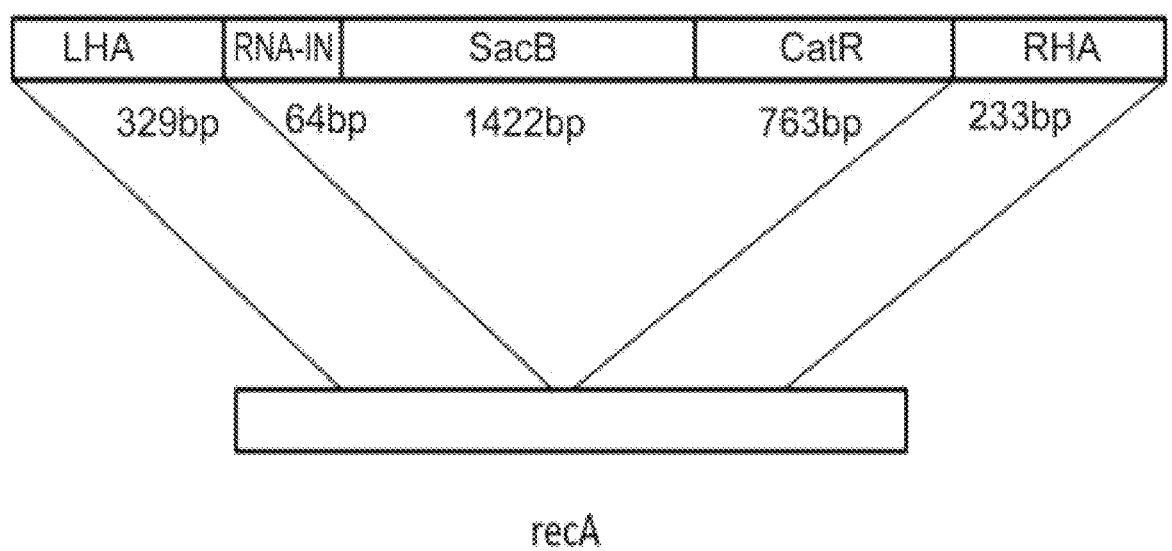
FIG. 2 shows the structure of the DNA fragment for homologous recombination in the region of gene recA of *Escherichia coli* for producing *Escherichia coli* strain SCS 110.
Figure 3A:
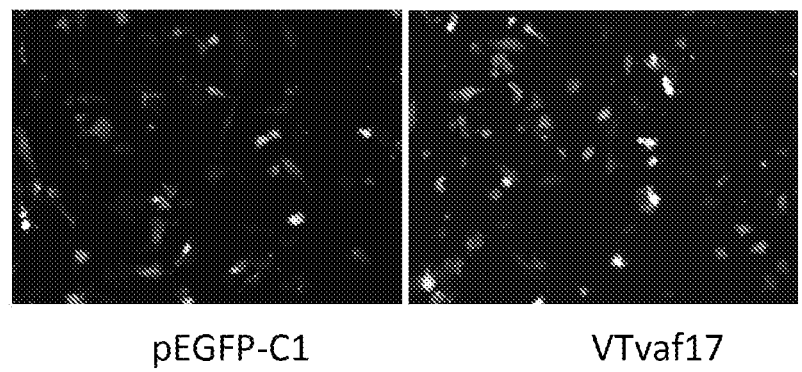
Figure 3B:
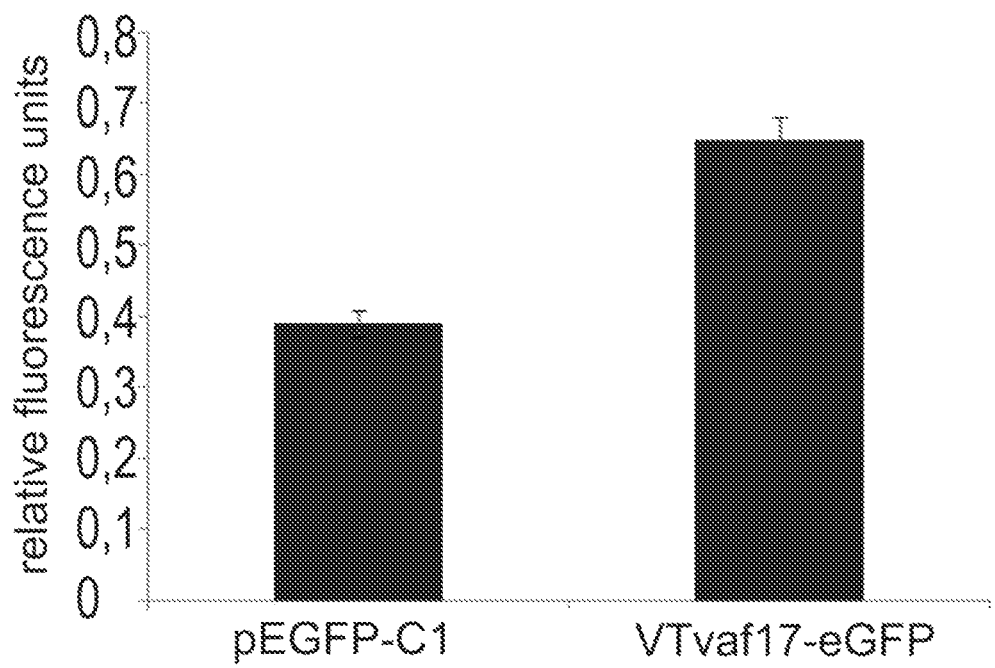

FIG. 3A demonstrates fluorescence microimaging of the HEK-293 cell culture 48 hours after the transfection of the cells with plasmid vector pEFGP-C1 (Clontech) and DNA vector VTvaf17-eGFP (A), and FIG. 3B is a diagram of fluorescence emitted by the protein extracted from HEK-293 cells 48 hours after the transfection of the cells with plasmid vector pEFGP-C1 (Clontech) and DNA vector VTvaf17-eGFP (B) for the purpose of comparing the levels of accumulation of the product of the target gene, e.g. green fluorescent protein (GFP), in the HEK-293 cells 48 hours after the transfection of the cells with plasmid vector pEFGP-C1 (Clontech) and DNA vector VTvaf17-eGFP.

Figure 4:
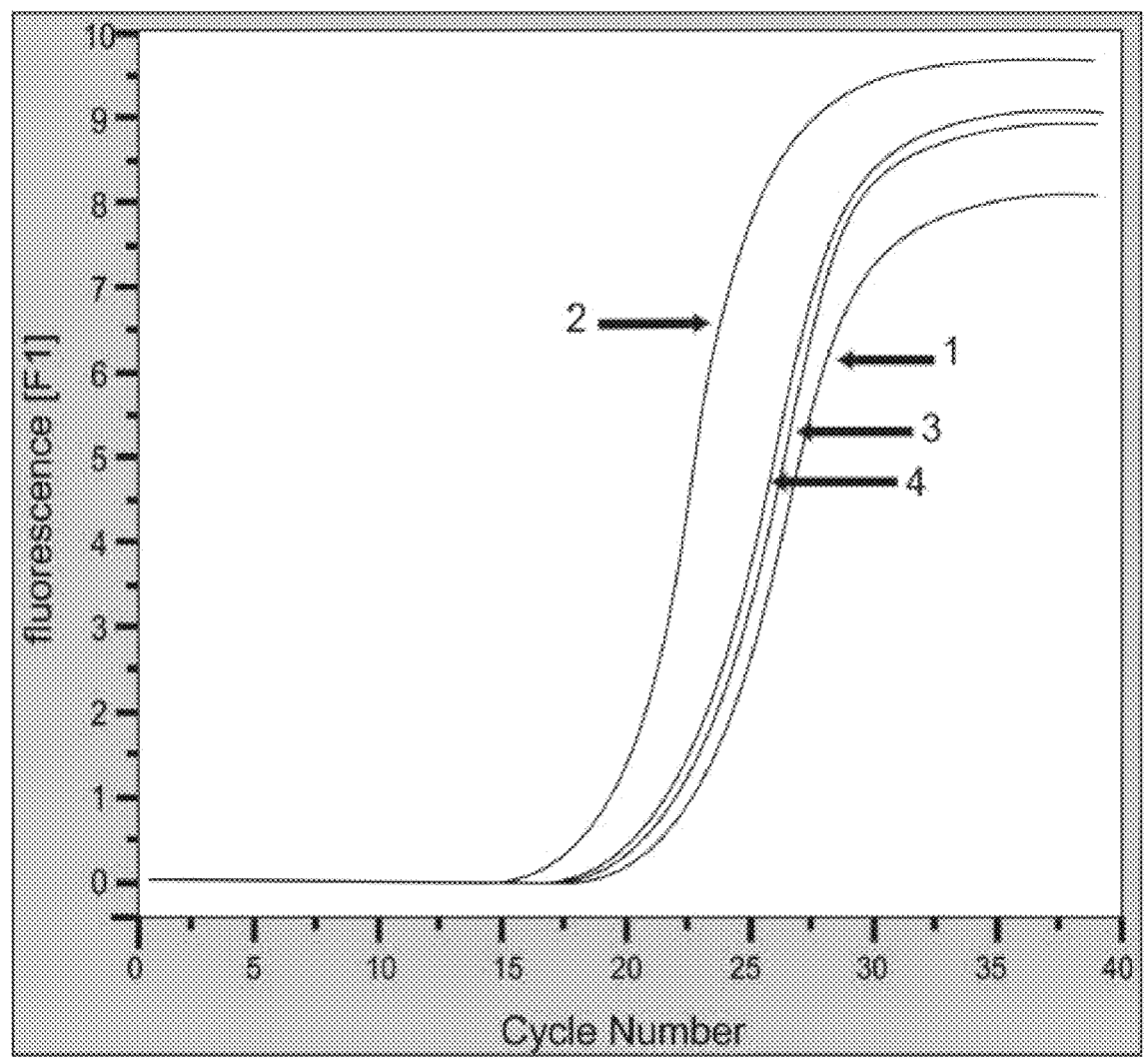

FIG. 4 shows the patterns of accumulation of elastin gene mRNA in keratinocyte cells HaCaT before the transfection and 48 hours after the transfection of these cells with DNA vector VTvaf17-ELN carrying a human elastin gene encoding region for the purpose of analysing changes in the accumulation of the target gene mRNA, e.g. mRNA of elastin gene, in keratinocyte cells HaCaT before the transfection and 48 hours after the transfection of these cells with DNA vector VTvaf17-ELN carrying a human elastin gene encoding region.

Figure 5:
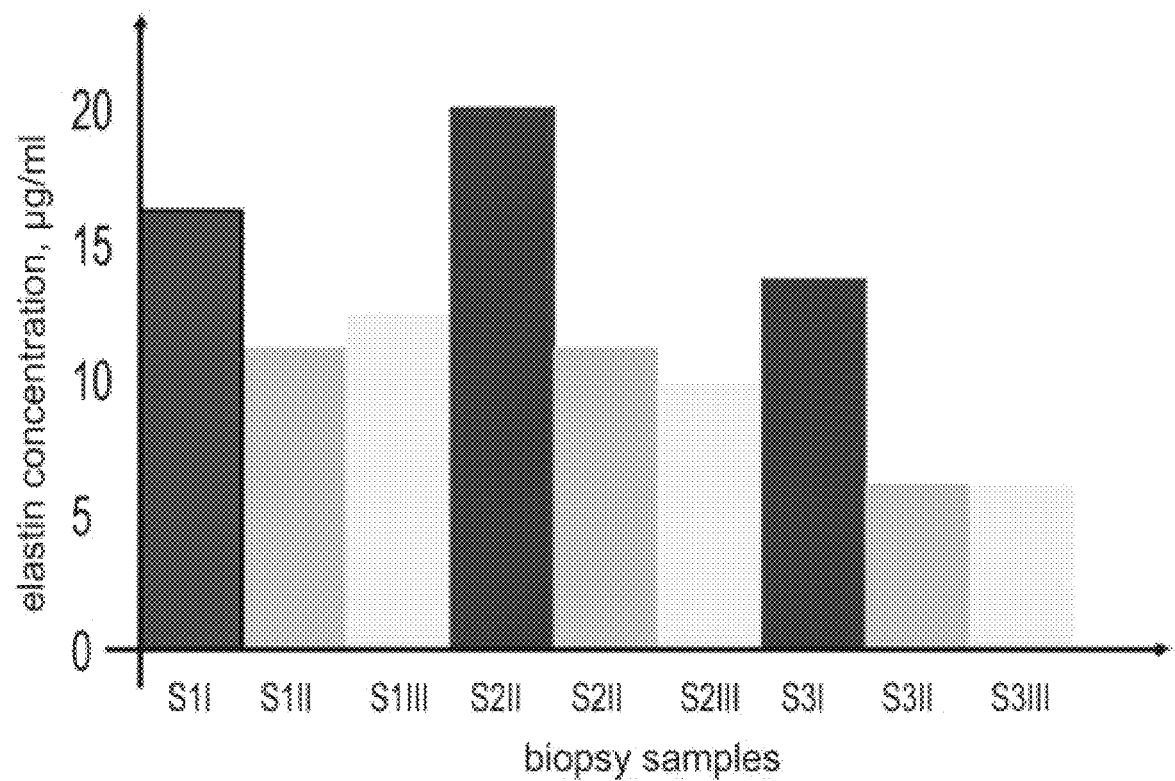

FIG. 5 shows the plot of elastin protein concentration in skin biopsy samples of three patients after the injection into the skin of these patients of gene therapy DNA vector VTvaf17-ELN carrying a human elastin gene encoding region for the purpose of analysing changes in elastin protein concentrations in human skin upon administration into human skin of gene therapy DNA vector VTvaf17 carrying the target gene, e.g. human elastin gene.

Figure 6:
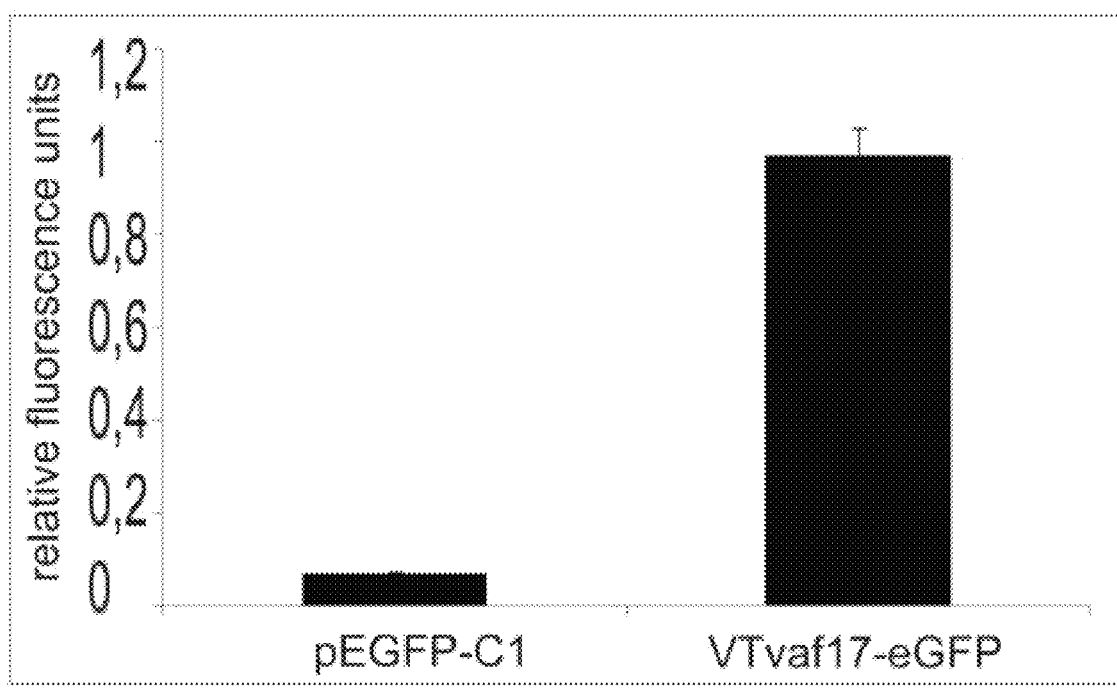

FIG. 6 shows a graph of changes in the concentration of green fluorescent protein (GFP) in bovine kidney cells MDBK 48 hours after cell transfection with DNA vector VTvaf17 and DNA vector VTvaf17-eGFP carrying a green fluorescent protein coding region for the purpose of comparing the levels of accumulation of the product of the target gene, e.g. green fluorescent protein (GFP), in bovine kidney cells MDBK 48 hours after cell transfection with DNA vector VTvaf17 and DNA vector VTvaf17-eGFP carrying a green fluorescent protein coding region.

FIG. 7 provides the DNA vector, VTvaf17, marked up to show its structural elements.

DETAILED DESCRIPTION OF THE PREFERRED EMBODIMENT OF THE INVENTION

The essence of the invention is explained in the following examples.

Example 1

Production of gene therapy DNA vector VTvaf17 containing the promoter of human elongation factor gene EF1A with an intrinsic enhancer, a polylinker, a transcription terminator and a polyadenylation sequence of the human growth hormone, regulatory element RNA-OUT of transposon Tn10, and an origin of replication with a single nucleotide substitution to increase plasmid production.

Gene therapy DNA vector VTvaf17 was constructed by consolidating six fragments of DNA derived from different sources:

(a) the origin of replication was produced by PCR amplification of a region of commercially available plasmid pBR322 with a point mutation using oligonucleotides Ori-F, Ori-R, Ori-M1, and Ori-M2 (SEQ ID NO: 3-6;

(b) the promoter region EF1a was produced by PCR amplification of a site of human genomic DNA using oligonucleotides EF1-F and EF1-R (SEQ ID NO: 7-8);

(c) the transcription terminator hGH-TA was produced by PCR amplification of a site of human genomic DNA using oligonucleotides hGH-F and hGH-R (SEQ ID NO: 9-10);

(d) the regulatory site RNA-OUT of transposon Tn10 was synthesized from oligonucleotides RO-F, RO-R, RO-1, RO-2, and RO-3 (SEQ ID NO: 11-15);

(e) the kanamycin resistance gene was produced by PCR amplification of a site of commercially available plasmid pET-28 using oligonucleotides Kan-F and Kan-R (SEQ ID NO: 16-17);

(f) the polylinker was produced by annealing two synthetic oligonucleotides MCS1 and MCS2 (SEQ ID NO: 17-18).

PCR amplification was performed using the commercially available kit Phusion® High-Fidelity DNA Polymerase (New England Biolabs) as per the manufacturer's instructions. The fragments have overlapping regions allowing for their consolidation with subsequent PCR amplification. Fragments (a) and (b) were consolidated using oligonucleotides Ori-F and EF1-R (SEQ ID NO: 3 and SEQ ID NO: 8), and fragments (c), (d) and (e) were consolidated using oligonucleotides hGH-F and Kan-R (SEQ ID NO: 9 and SEQ ID NO: 17). Afterwards, the produced sites were consolidated by restriction with subsequent ligation by sites BamHI and NcoI. This resulted in a plasmid still devoid of the polylinker. To introduce it, the plasmid was cleaved by sites BamHI and EcoRI followed by ligation with fragment (f). Therefore, a 4182-bp vector was constructed carrying the kanamycin resistance gene flanked by SpeI restriction sites. Then this site was cleaved by SpeI restriction sites and the remaining fragment was ligated to itself. This resulted in a 3165-bp gene therapy DNA vector VTvaf17, which is recombinant and allows for antibiotic-free selection (SEQ ID NO: 1).

Example 2

To prove the efficiency of DNA vector VTvaf17, the target gene, e.g. the green fluorescent protein (GFP) gene, was cloned to the polylinker.

Production of gene therapy DNA vector VTvaf17-eGFP carrying a site coding the target gene, e.g. the gene coding green fluorescent protein (GFP). The coding region of the green fluorescent protein gene was produced by PCR amplification of commercially available plasmid pEGFP-C1 (Clontech) using oligonucleotides MVGFP-F and MVGFP-R (SEQ ID NO: 32-33). The produced PCR fragment was cleaved by restriction endonucleases BamHI and EcoRI, and ligated with a 4182-bp DNA vector carrying the kanamycin resistance gene and cleaved by the same enzymes. Further on, the kanamycin resistance gene was removed from the vector produced, as described in Example 1. This resulted in a 3874-bp DNA vector VTvaf17-eGFP allowing for antibiotic-free selection.

Example 3

To prove the efficiency of DNA vector VTvaf17, the target gene, e.g. the human elastin encoding gene, was cloned to the polylinker.

Production of DNA vector VTvaf17-ELN carrying a region coding the target gene, e.g. the human elastin encoding gene. The 2175-bp long coding region of the elastin gene (SEQ ID NO: 2) was produced by extracting total RNA from the patient's skin biopsy sample with subsequent reverse transcription and PCR amplification. The material was sampled from intact skin in area of the forearm, using the skin biopsy device Epiteasy 3.5 (Medax SRL). The patient's skin was preliminarily rinsed with sterile saline and anaesthetized with a lidocaine solution. The size of the biopsy sample was ca. 2×2×2 mm, and the weight was up to 20 mg. The sample was placed in 1 ml of Trizol Reagent (ThermoFisher Scientific), homogenized and heated for 5 minutes at 65° C. The sample was centrifuged at 14 000 g for 10 minutes and heated again for 10 minutes at 65° C. Then 200 μl of chloroform was added, and the mixture was gently stirred and centrifuged at 14 000 g for 10 minutes. Then the water phase was isolated and mixed with 1/10 of the volume of 3M sodium acetate, pH 5.2, and an equal volume of isopropyl alcohol. The sample was incubated at −20° C. for 10 minutes and then centrifuged at 14 000 g for 10 minutes. The packed cells were rinsed in 1 ml of 70% ethyl alcohol, air-dried and dissolved in 10 μl of RNase-free water. To synthesize the first strand of cDNA of the human elastin gene, Mint reverse transcriptase (Evrogen, Russia) was used. 4 μl of Mint Buffer, 2 μl of dithiothreitol, 2 μl of dNTP Mix, 2 μl of each of oligonucleotides ELN-F and ELN-R (SEQ ID NO: 34-35), and 2 μl of Mint reverse transcriptase were added to 6 μl of total RNA, and the mixture was incubated at 42° C. for 2 hours. The synthesized cDNA was used as a matrix in PCR amplification using oligonucleotides ELN-F and ELN-R (SEQ ID NO: 34-35), which was performed at 94° C. for 3 minutes; 30 cycles: at 94° C. for 20 seconds, at 60° C. for 20 seconds and at 72° C. for 60 seconds, with final elongation at 72° C. for 5 minutes. The produced PCR fragment was cleaved by restriction endonucleases BamHI and EcoRI, and ligated with a 4182-bp vector carrying the kanamycin resistance gene and cleaved by the same enzymes. Further on, the kanamycin resistance gene was removed from the vector produced, as described in Example 1. This resulted in a 5322-bp gene therapy DNA vector VTvaf17-ELN carrying a region encoding the elastin gene and allowing for antibiotic-free selection.

Example 4

Engineering of *Escherichia coli* strain SCS 110-AF for the production of gene therapy DNA vector VTvaf17 and gene therapy vectors based on it.

Escherichia coli strain SCS 110-AF for the engineering of gene therapy DNA vector VTvaf17 and gene therapy vectors based on it was produced by homologous recombination by administering to its chromosome, specifically to the region of gene recA, of the linear fragment which contains regulatory element RNA-IN of transposon Tn10 allowing for antibiotic-free positive selection (64-bp), levansucrase gene sacB the product of which ensures selection within a sucrose-containing medium (1422-bp), chloramphenicol resistance gene catR required for the picking of strain clones in which homologous recombination occurred (763-bp), and two homologous sequences (homology arms) ensuring homologous recombination in the region of gene recA concurrent with gene inactivation (329-bp and 233-bp for the left arm and for the right arm, respectively).

To synthesize the left and the right homology arms, fragments of gene recA were subject to PCR amplification using the genomic DNA of *Escherichia coli* SCS 110 (Agilent Technologies) as a matrix. To synthesize the left homology arm, primers LHA-F and LHA-R (SEQ ID NO: 20-21) were used, while for synthesizing the right homology arm primers RHA-F and RHA-R (SEQ ID NO: 30-31) were used. The RNA-IN fragment was tailed with synthetic oligonucleotides IN-F, IN-1, IN-2, IN-R (SEQ ID NO: 22-25). The gene sacB was produced by PCR amplification using the genomic DNA *B. subtilis* 168HT as a matrix, and SacB-F and SacB-R as primers (SEQ ID NO: 26-27). To synthesise the gene catR, PCR amplification was performed using *Escherichia coli* strain BL21 pLysS as a matrix, and CatR-F and CatR-R (SEQ ID NO: 28-29) as primers. PCR products LHA (the left homology arm), SacB, and RHA (the right homology arm) were amplified at 94° C. for 3 minutes; 30 cycles: at 94° C. for 20 seconds, at 60° C. for 20 seconds and at 72° C. for 60 seconds, with final elongation at 72° C. for 5 minutes. PCR product RNA-IN was synthesized at 94° C. for 3 minutes; 30 cycles: at 94° C. for 10 seconds, at 60° C. for 10 seconds and at 72° C. for 10 seconds, using oligonucleotides IN-F, IN-1, IN-2, IN-R (SEQ ID NO: 22-25) for the assembly of the fragment. For this, 10 µM of primers IN-F and IN-R, and 5 µM of primers IN-1 and IN-2 was used. PCR amplification was performed using the commercially available kit Phusion® High-Fidelity DNA Polymerase (Thermo Fisher Scientific) as per the manufacturer's instructions.

The linear fragment for homologous recombination was synthesized by consolidating five PCR products. All of the five products had overlapping areas allowing for subsequent assembly into a single fragment. All fragments were mixed in aliquots of 10 ng in a volume of 50 µl. The PCR product was derived at 94° C. for 3 minutes; 10 cycles: at 94° C. for 30 seconds, at 60° C. for 30 seconds and at 72° C. for 2 minutes, without primers added. Then primers LHA-F, RHA-R (SEQ ID NO: 20-21) were added, and 25 more PCR cycles were performed: at 94° C. for 30 seconds, at 60° C. for 30 seconds and at 72° C. for 2 minutes, with final elongation at 72° C. for 5 minutes. This resulted in a 2811-bp long PCR fragment having the following structure: LHA-RNA-IN-SacB-CatR-RHA. This fragment was recovered preparatively from agarose gel using the DNA Elution Kit (BioSilica, Russia) according to the manufacturer's instructions.

To synthesize *Escherichia coli* strain SCS 110-AF, electrocompetent cells were prepared. To do this, a single colony of *Escherichia coli* strain SCS 110 (Agilent Technologies) was used to infect 10 ml of LB broth, and the cells were cultured overnight in an orbital shaker at 150 rpm and 37° C. On the following day, 1/20 was re-plated into 100 ml of LB broth and cultured in an orbital shaker at 150 rpm and 37° C. to reach $OD_{600}$=0.5. Upon reaching the required optical density, the cells were cooled down to 0° C. and centrifuged for 10 minutes at 4000 g. Then the medium was removed, and the cells were rinsed with 100 ml of ice-cold bidistilled water twice to remove the remaining medium and then rinsed with 20 ml of 10% glycerine. After that, the cells were re-suspended in 1 ml of 10% glycerine and used for transformation.

Transformation with the produced linear fragment was performed by electroporation in 1 mm cuvettes at 2 kV, 200 Ohm, 25 µF using the Gene Pulser Xcell (Bio-Rad, USA). The duration of the pulse was 4.9 ms to 5.1 ms. After that, the cells were cultivated in a SOC medium for 2.5 hours in an incubator shaker at 30° C. Then the cells were poured into LB agar plates (Petri dishes) containing 10 µg/ml of chloramphenicol. The cells were cultivated for 48 hours at 30° C. The picked-out clones were tested for survival in a selective medium containing yeastrel, peptone, 6% sucrose, and 10 µg/ml of chloramphenicol. The genotype of the resulting strain is recA rpsL (Strr) thr leu endA thi-1 lacY galK galT ara tonA tsx dam dcm supE44 Δ(lac-proAB) [F" traD36 proAB lacIq ZΔM15]ChmR sacB+

Example 5

Construction of *Escherichia coli* strain SCS110-AF/VTvaf17 (registered at the Russian National Collection of Industrial Microorganisms under number B-12990, INTERNATIONAL DEPOSITARY AUTHORITY No. NCIMB 42801) carrying gene therapy DNA vector VTvaf17 for its further development.

To prepare electrocompetent cells of *Escherichia coli* strain SCS110-AF, a single colony was used to infect 10 ml of LB broth, and the cells were cultured overnight in an orbital shaker at 150 rpm and 37° C. On the following day, 1/20 was re-plated into 100 ml of LB broth and cultured in an orbital shaker at 150 rpm and 37° C. to reach $OD_{600}$=0.5. Upon reaching the required optical density, the cells were cooled down to 0° C. and centrifuged for 10 minutes at 4000 g. Then the medium was removed, and the cells were rinsed with 100 ml of ice-cold bidistilled water twice to remove the remaining medium and then rinsed with 20 ml of 10% glycerine. After that, the cells were re-suspended in 1 ml of 10% glycerine and used for transformation by electroporation. Electroporation was performed in 1 mm cuvettes at 2 kV, 200 Ohm, 25 µF using the Gene Pulser Xcell (Bio-Rad, USA). The duration of the pulse was 4.9 ms to 5.1 ms, and 1-10 ng of the vector was used. After that, the cells were cultivated in a SOC medium for 2.5 hours in an incubator shaker at 30° C. Then the cells were poured into agar plates (Petri dishes) with a selective medium containing yeastrel, peptone, 6% sucrose, and 10 µg/ml of chloramphenicol. This procedure resulted in the production of *Escherichia coli* strain SCS110-AF/VTvaf17 (registered at the Russian National Collection of Industrial Microorganisms under number B-12990, INTERNATIONAL DEPOSITARY AUTHORITY No. NCIMB 42801) carrying gene therapy DNA vector VTvaf17. 48 hours later, a single colony was used to infect 10 ml of a liquid selective medium containing yeastrel, peptone, 6% sucrose, and 10 µg/ml of chloramphenicol, and the medium was cultivated overnight in an orbital shaker at 150 rpm and 37° C. On the following day, the cells were pelleted, and DNA vector was extracted by alkaline lysis using GeneJET Plasmid Miniprep Kit (Thermo Fisher Scientific) according to the manufacturer's instructions.

Example 6

To prove the efficiency of gene therapy DNA vector VTvaf17, the target gene, e.g. the green fluorescent protein (GFP) coding gene, was cloned to the polylinker.

Comparison of levels of accumulation of the target gene, e.g. the green fluorescent protein (GFP), in HEK-293 cells 48 hours after cell transfection with plasmid vector pEFGP-C1 (Clontech) and gene therapy DNA vector VTvaf17-eGFP.

To measure the level of accumulation of the green fluorescent protein (GFP), in HEK-293 cells (human embryonic kidney cells transformed with adenovirus 5 DNA, ATCC CRL-1573), transfection of the cells with plasmid vector pEFGP-C1 (Clontech) and gene therapy DNA vector VTvaf17-eGFP was performed.

The cells were grown in a DMEM medium (ThermoFisher Scientific, USA) containing 10% fetal bovine serum (ThermoFisher Scientific, USA), 4.5 g/l of glucose and 10 µg/ml of gentamicin, with a 5% $CO_2$ overlay at 37° C. To achieve 90% confluence, 24 hours before the transfection procedure the cells were seeded into a 24-well plate in the quantity of $4*10^4$ cells per well. Lipofectamine 3000 (ThermoFisher Scientific, USA) was used as a transfection reagent. In test tube 1, 1 µl of the solution of plasmid vector pEFGP-C1 and gene therapy DNA vector VTvaf17-eGFP (500 ng/µl each) and 1 µl of reagent P3000 were added to 25 µl of medium Opti-MEM (Gibco). The preparation was mixed by gentle shaking. In test tube 2, 1 µl of solution Lipofectamine 3000 was added to 25 µl of medium Opti-MEM (Gibco). The preparation was mixed by gentle shaking. The contents from test tube 1 were added to the contents of test tube 2, and the mixture was incubated at room temperature for 5 minutes. The resulting solution was added dropwise to the cells in the volume of 40 µl.

The results were recorded 48 hours later using the Olympus ix53 fluorescence microscope (Japan) with a 485/535 nm filter set (FIG. 3A). These results demonstrate that the transfection of HEK-293 cells with gene therapy DNA vector VTvaf17-eGFP causes a significant increase in the accumulation of the green fluorescent protein as opposed with the transfection of the same cells with plasmid vector pEFGP-C1 (Clontech).

The results were recorded by measuring fluorescence of the protein extracted from the transfected cell line. To do this, the cells were rinsed from the well by pipetting and pelleted at 6000 rpm for 10 minutes, rinsed twice, and then the packed cells were re-suspended in 1 ml of sodium phosphate buffer. The cells were lysed in three freeze/thaw cycles at −70° C. Then the homogenate of lysed cells was pelleted at 13000 g for 15 minutes. Supernatants were transferred into a 96-well culture plate (Grainer Bio-one) in four replicates for each sample, and then relative fluorescence of GFP was measured (absorption 455 nm/emission 538 nm) using Fluoroskan Ascent Microplate Fluorometer (Labsystems). The resulting values were normalized according to the total protein concentration in the sample, which was measured by the Bradford protein assay. To do this, Coomassie Brilliant Blue R-250 was used as a dye. Each replicate was diluted in the wells of the 96-well plate (4 replicates for each sample) with water by a factor of 100, and then the dye was added. After that, optical density of all samples was measured at 620 nm using Multiskan Ascent (Thermo). The resulting values were compared with the calibration curve constructed for bovine serum albumin (Bio-Rad) with a series of sequential dilutions from 20 to 2.5 µg/ml. Calculations were made using the following formula:

$$\Sigma\text{protein content }(\mu g)=\{[x]-\sigma\}\div k*M,$$

where [x] is the mean value of $OD_{620}$ of the four replicates for each sample, σ—mean deviation, k is the slope coefficient of the calibration curve for BSA, M is the dilution factor of the sample.

Based on the values of the total concentration of protein extracted from the cells, GFP fluorescence in the samples was normalized using the following formula:

$$OEn=[OE]\div\Sigma\text{protein content (mg)}$$

Where

[OE] is the average of the four replicates for each sample, in relative fluorescence units (RFU).

The results are shown in FIG. 3B and demonstrate that the transfection of HEK-293 cells with gene therapy DNA vector VTvaf17-eGFP doubles the level of accumulation of the green fluorescent protein as opposed with the transfection of the same cells with plasmid vector pEFGP-C1 (Clontech).

Example 7

To prove the efficiency of gene therapy DNA vector VTvaf17, the target gene, e.g. the elastin encoding gene, was cloned to the polylinker.

Analysis of the changes in the accumulation of mRNA of the target gene, e.g. the elastin gene, in keratinocyte cells HaCaT 48 hours after the transfection of these cells with DNA vector VTvaf17-ELN carrying a human elastin gene encoding region.

The HaCaT cells (immortalized human keratinocytes, ThermoFisher Scientific, USA) were grown in a DMEM medium (ThermoFisher Scientific, USA) containing 10% fetal bovine serum (ThermoFisher Scientific, USA), 4.5 g/l of glucose and 2 mM of glutamine, with a 5% $CO_2$ overlay at 37° C. To achieve 90% confluence, 24 hours before the transfection procedure the cells were seeded into a 24-well plate in the quantity of $5*10^4$ cells per well. Lipofectamine 3000 (ThermoFisher Scientific, USA) was used as a transfection reagent. The transfection of the cells with gene therapy DNA vector VTvaf17-ELN expressing the human elastin gene was performed according to the procedure described in Example 6. HaCaT cells transfected with gene therapy DNA vector VTvaf17 were used as a reference. Extraction of total RNA from the transfected cells and construction of the first cDNA strand was performed according to the procedure described in Example 3. To measure the level of expression of elastin gene mRNA after transfection, real-time PCR (SYBR Green Real Time PCR) was used. For the amplification of human elastin cDNA, oligonucleotides EL1F and EU R were used (see SEQ ID NO: 36-37). The length of the amplification product is 227 bp. Beta-2 microglobulin (B2M) was used as a reference gene.

PCR amplification was performed with the use of QuantiTect SYBR Green RT-PCR Kit (Qiagen, USA) or another real-time PCR kit in 20 µl of the amplification mixture containing 25 µl of QuantiTect SYBR Green RT-PCR Master Mix, 2.5 mM of magnesium chloride, 0.5 µM of each primer, and 5 µl of total RNA. For amplification CFX96 reaction module (Bio-Rad, USA) was used under the following conditions: 1 cycle of reverse transcription at 42° C. for 30 minutes, denaturation at 98° C. for 15 minutes, followed by 40 cycles comprising denaturation at 94° C. for 15 s, annealing of primers at 60° C. for 30 s and elongation at 72° C. for 30 s. Positive control included amplicons from PCR on matrices represented by plasmids in known concentrations containing cDNA sequences of the genes ELN and B2M. Negative control included deionized water. Real-time quantification of the PCR products, i. e. ELN and B2M gene cDNAs obtained by amplification, was conducted using the Bio-Rad CFX Manager 2.1 software.

To demonstrate increased expression of the ELN gene in human keratinocyte cells after the transfection of these cells with gene therapy DNA vector VTvaf17-ELN carrying a region encoding the elastin gene, FIGS. 3A and 3B demonstrate accumulation of PCR products corresponding to the following:

1—cDNA of ELN gene after transfection with gene therapy vector VTvaf17;

2—cDNA of ELN gene after transfection with gene therapy vector VTvaf17-ELN carrying the elastin gene coding region;

3—cDNA of B2M gene after transfection with gene therapy vector VTvaf17;

4—cDNA of B2M gene after transfection with gene therapy vector VTvaf17-ELN carrying the elastin gene coding region.

It follows from the figure that transfection with gene therapy DNA vector VTvaf17-ELN carrying the target gene, e.g. the human elastin gene, causes the level of human elastin gene specific cDNA to rise massively.

Example 8

To prove the efficiency of gene therapy DNA vector VTvaf17, the target gene, e.g. the elastin encoding gene, was cloned to the polylinker.

Measurements were made of the changes in the concentration of the elastin protein in human skin upon injection of gene therapy DNA vector VTvaf17 carrying the target gene, e.g. the human elastin gene, into human skin.

To analyse changes in the concentration of the elastin protein, gene therapy DNA vector VTvaf17-ELN carrying a region encoding the elastin gene was injected into the forearm skin of three patients featuring visible age-specific changes, with concurrent introduction of a placebo being gene therapy DNA vector VTvaf17 devoid of the ELN gene cDNA. Patient 1, female, 56 years old, ageing characterised by fine lines (P1); Patient 2, female, 67 years old, ageing characterised by deformation or deep furrows (P2); Patient 3, male, 60 years old, ageing characterised by deformation (P3).

Gene therapy DNA vector VTvaf17 (placebo) and gene therapy DNA vector VTvaf17-ELN carrying a region encoding the elastin gene were injected in the quantity of 1 mg for each of the genetic constructs using the tunnel method with a 30G needle to the depth of 3 mm. The volume of the injected solution of gene therapy DNA vector VTvaf17 (placebo) and gene therapy DNA vector VTvaf17-ELN carrying a region encoding the elastin gene is 0.3 ml for each of the genetic constructs. The points of introduction of each of the genetic constructs were located at 5 to 10 cm intervals.

The biopsy samples were taken on the $2^{nd}$ day after the introduction of the gene therapy DNA vectors. The biopsy samples were taken from the patients' skin in the area of the introduction of gene therapy DNA vector VTvaf17-ELN carrying a region encoding the elastin gene (I), gene therapy DNA vector VTvaf17 (placebo) (II), and from intact skin (III), using the skin biopsy device Epitheasy 3.5 (Medax SRL). The skin of the patients was preliminarily rinsed with sterile saline and anaesthetized with a lidocaine solution. The size of the biopsy sample was ca. 2×2×2 mm, and the weight was up to 10 mg. The sample was placed in a buffer solution containing 50 mM of Tris-HCl, pH 7.6, 100 mM of NaCl, 1 mM of EDTA and 1 mM of phenylmethylsulphonyl fluoride, and homogenized to obtain a homogenized suspension. The suspension was then centrifuged for 10 minutes at 14,000 g. Supernatant was collected and used to assay the target protein.

The elastin protein in the patients' skin biopsy samples was quantified by enzyme-linked immunosorbent assay using the Enzyme-Linked Immunosorbent Assay Kit For Elastin (ELN) (SEB337Hu, Cloud-Clone Corp., USA).

From the kit, highly specific antibodies to elastin protein adsorbed to microplate wells were used. 100 µl of each of the diluted reference samples and tested samples were added to the wells and incubated for 2 hours at 37° C. Then 100 µl of reagent A was added, the plate was covered with adhesive tape and incubated for 1 hour at 37° C. Then the wells were rinsed three times with 350 µl of wash buffer and 100 µl of reagent B was added with subsequent incubation for 30 minutes at 37° C. After incubation, the wells were washed five times with 350 µl of wash buffer, 90 µl of substrate solution was added and incubated for 20-25 minutes at 37° C. The reaction was terminated by adding 50 µl of inhibitor removal buffer and optical density was measured at 450 nm using the fully automated analyser for biochemistry and enzyme-linked assays ChemWell (Awareness Technology Inc., USA). To measure the numerical value of concentration, the calibration curve constructed using the reference samples from the kit with known concentrations of the elastin protein was used. R-3.0.2 was used for the statistical treatment of the results and data visualization (www.r-project.org/).

The skin of each of the three patients demonstrates an increased concentration of the elastin protein in the area of introduction of gene therapy DNA vector VTvaf17 carrying the target gene, e.g. the human elastin gene, compared to the concentration of the elastin protein in the area of introduction of gene therapy DNA vector VTvaf17 (placebo) devoid of the region encoding the human elastin gene. The resulting values of elastin concentrations in the skin of patients P1, P2 and P3 are shown in FIG. 5.

Example 9

To prove the efficiency of gene therapy DNA vector VTvaf17, the target gene, e.g. the green fluorescent protein (GFP) encoding gene in bovine kidney cells MDBK, was cloned to the polylinker.

The levels of accumulation of the target gene, e.g. the green fluorescent protein (GFP), in bovine kidney cells MDBK 48 hours after cell transfection with gene therapy DNA vector VTvaf17-eGFP were compared.

To quantify the level of accumulation of the green fluorescent protein (GFP) in MDBK cells (bovine kidney cells, ATCC CLL-22), the cells were transfected with gene therapy DNA vector VTvaf17-eGFP.

The cells were grown in a MEM medium (ThermoFisher Scientific, USA) containing 10% fetal bovine serum (ThermoFisher Scientific, USA), 1 g/l of glucose and 2 mM of glutamine, with a 5% $CO_2$ overlay at 37° C. To achieve 90% confluence, 24 hours before the transfection procedure the cells were seeded into a 24-well plate in the quantity of $3*10^4$ cells per well. Lipofectamine 3000 (ThermoFisher Scientific, USA) was used as a transfection reagent. Transfection was performed according to the procedure described in Example 6. Recombinant gene therapy vector VTvaf17 free of the green fluorescent protein gene was used as a reference. The results were recorded by measuring fluorescence of the protein extracted from the transfected cell line, as described in Example 6.

The results are shown in FIG. 6 and allow us to conclude that the transfection of the bovine kidney cell line MDBK with gene therapy DNA vector VTvaf17-eGFP carrying the green fluorescent protein gene leads to a higher level of accumulation of the green fluorescent protein comparing with the transfection of the same cells with gene therapy vector VTvaf17 devoid of the green fluorescent protein gene.

Example 10

To prove the producibility and constructability of gene therapy DNA vector VTvaf17 on an industrial scale, large-scale fermentation of *Escherichia coli* strain SCS110-AF/VTvaf17 (registered at the Russian National Collection of Industrial Microorganisms under number B-12990, INTERNATIONAL DEPOSITARY AUTHORITY No. NCIMB 42801) carrying gene therapy DNA vector VTvaf17 was performed.

Fermentation of *Escherichia coli* strain SCS110-AF/VTvaf17 carrying gene therapy DNA vector VTvaf17 was performed in a 10-l bioreactor/fermenter with subsequent extraction of gene therapy DNA vector VTvaf17.

For the fermentation of *Escherichia coli* strain SCS110-AF/VTvaf17 a medium was prepared containing (per 10 l of volume) 100 g of tryptone, 50 g of yeastrel (Becton Dickinson), then the medium was diluted with water to 8800 ml and autoclaved at 121° C. for 20 minutes, and then 1200 ml of 50% (weight to volume) sucrose was added. After that, the seed culture of *Escherichia coli* strain SCS110-AF/VTvaf17 was inoculated into a culture flask in the volume of 100 ml. The culture was incubated in an incubator shaker for 16 hours at 30° C. the seed culture was transferred to the Techfors S bioreactor (Infors HT, Switzerland) and grown to a stationary phase. The process was controlled by measuring optical density of the culture at 600 nm. The cells were pelleted for 30 minutes at 5000-10000 g. Supernatant was removed, and the cell pellet was re-suspended in 10% (by volume) phosphate buffered saline. The cells were centrifuged again for 30 minutes at 5000-10000 g. Supernatant was removed, a solution of 20 mM Tris-HCl, 1 mM EDTA, 200 g/l sucrose, pH 8.0, was added to the cell pellet in the volume of 1000 ml, and the mixture was stirred thoroughly to a homogenized suspension. Then egg lysozyme solution was added to the final concentration of 100 μg/ml. The mixture was incubated for 20 minutes on ice while stirring gently. Then 2500 ml of 0.2 M NaOH, 10 g/l sodium dodecyl sulphate (SDS) was added, the mixture was incubated for 10 minutes on ice while stirring gently, then 3500 ml of 3M sodium acetate, 2M acetic acid, pH 5-5.5 was added, and the mixture was incubated for 10 minutes on ice while stirring gently. The resulting sample was centrifuged for 20-30 minutes at 15000 g or a greater value. The solution was decanted delicately, and residual precipitate was removed by passing through a coarse filter (filter paper). Then RNase A (Sigma) was added to the final concentration of 20 μg/ml, and the solution was incubated overnight for 16 hours at room temperature. The solution was then centrifuged for 20-30 minutes at 15000 g and passed through a 0.45 μm membrane filter (Millipore). Then ultrafiltration was performed with a membrane of 100 kDa (Millipore) and the mixture was diluted to the initial volume with a buffer solution of 25 mM Tris-HCl, pH 7.0. This manipulation was performed three to four times. The solution was applied to the column with 250 ml of DEAE Sepharose HP (GE, USA), equilibrated with 25 mM Tris-HCl, pH 7.0. After the application of the sample, the column was washed with three volumes of the same solution and then gene therapy DNA vector VTvaf17 was eluted using a linear gradient of 25 mM Tris-HCl, pH 7.0, to obtain a solution of 25 mM Tris-HCl, pH 7.0, 1M NaCl, five times the volume of the column. The elution process was controlled by measuring optical density of the run-off solution at 260 nm. Chromatographic fractions containing gene therapy DNA vector VTvaf17 were joined together and subjected to gel filtration using Superdex 200 (GE, USA). The column was equilibrated with phosphate buffered saline. The elution process was controlled by measuring optical density of the run-off solution at 260 nm, and the fractions were analysed by agarose gel electrophoresis. Chromatographic fractions containing gene therapy DNA vector VTvaf17 were joined together and kept at −20° C. The yield is sufficient for large-scale industrial production of gene therapy DNA vector VTvaf17.

Therefore, the purpose of this invention, specifically the construction of a gene therapy DNA vector for genetic modification of human and animal cells, which would reasonably combine:

V) possibility of safe use in the gene therapy of human beings and animals due to the absence of antibiotic resistance genes in the gene therapy DNA vector;

VI) length that ensures efficient gene delivery to the target cell;

VII) presence of regulatory elements that ensure efficient expression of the target genes while not being represented by nucleotide sequences of viral genomes; and VIII) producibility and constructability on an industrial scale, has been achieved, which is supported by the following examples: for Item I—Example 1; for Item II—Examples 1, 6, 7, 8; 9; for Item III—Examples 1, 6, 7, 8, 9; for Item IV—Examples 5, 10.

INDUSTRIAL APPLICABILITY

All the examples listed above support industrial applicability of the proposed gene therapy DNA vector VTvaf17 and the method of its production, the genetically modified strain *Escherichia coli* SCS110-AF for the construction of DNA vector VTvaf17 and gene therapy DNA vectors carrying target genes based on it, and the method of production of *Escherichia coli* strain SCS110-AF, the genetically modified strain *Escherichia coli* SCS110-AF/VTvaf17 (registered at the Russian National Collection of Industrial Microorganisms under number B-12990, INTERNATIONAL DEPOSITARY AUTHORITY No. NCIMB 42801) carrying gene therapy DNA vector VTvaf17 for the construction of it, and the method of production of *Escherichia coli* strain SCS110-AF/VTvaf17.

List of Abbreviations

VTvaf17—Gene therapy vector that does not contain sequences of viral genomes and antibiotic resistance markers (vector therapeutic virus-antibiotic-free)
DNA—Deoxyribonucleic acid
cDNA—Complementary deoxyribonucleic acid
RNA—Ribonucleic acid
mRNA—Messenger ribonucleic acid bp—base pair
PCR—Polymerase chain reaction
ml—millilitre, μl—microlitre
l—litre
μg—microgram
mg—milligram
g—gram
μmol—micromol
mM—millimol
min—minute
s—second
rpm—rotations per minute
nm—nanometre
cm—centimetre
mW—milliwatt RFU—Relative fluorescence unit
PBS—Phosphate buffered saline It is hereby certified that the deposit(s) (registered at the Russian National Collection of Industrial Microorganisms under number B-12990, INTERNATIONAL DEPOSITARY AUTHORITY No. NCIMB 42801) were made in compliance with the terms of the Budapest Treaty and that: (a) during the pendency of this application, access to the deposited organisms will be afforded to the Commissioner upon request; (b) all restrictions upon availability to the public of the deposited materials will be irrevocably removed upon granting of the patent, subject to 37 C.F.R. Section 1.808(b); (c) the deposit will be maintained for a period of 30 years or 5 years after the last request or for the effective life of the patent, whichever is longer; and (d) the deposit will be replaced if it should ever become non-viable.

What is claimed is:

1. A gene therapy DNA vector, VTvaf17, comprising the nucleic acid sequence depicted in SEQ ID NO: 1.

2. An *Escherichia coli* strain SCS 110-AF transformed with a vector comprising the nucleic acid sequence depicted in SEQ ID NO: 1.

3. An *Escherichia coli* strain SCS 110-AF/VTvaf17, said strain comprising the gene therapy DNA vector, VTvaf17, comprising the nucleic acid sequence depicted in SEQ ID NO: 1.

* * * * *